(12) United States Patent
Kobayashi et al.

(10) Patent No.: US 6,614,514 B2
(45) Date of Patent: Sep. 2, 2003

(54) DISTORTION MEASURING APPARATUS AND DISTORTION MEASURING METHOD USING THIS APPARATUS

(75) Inventors: Kazunaga Kobayashi, Sakura (JP); Masahiro Kusakari, Sakura (JP); Shimei Tanaka, Sakura (JP); Matsuhiro Miyamoato, Sakura (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 10/123,810

(22) Filed: Apr. 15, 2002

(65) Prior Publication Data

US 2003/0035099 A1 Feb. 20, 2003

(30) Foreign Application Priority Data

Jul. 16, 2001 (JP) ........................................ 2001-215887

(51) Int. Cl.⁷ .............................................. G01N 21/00
(52) U.S. Cl. ...................................................... 356/73.1
(58) Field of Search ........................ 356/73.1, 44, 301; 250/227.11–227.32

(56) References Cited

U.S. PATENT DOCUMENTS 4,823,166 A * 4/1989 Hartog et al. .................. 356/44
5,943,123 A * 8/1999 Oshimi et al. ............. 356/73.1

* cited by examiner

*Primary Examiner*—Tu T. Nguyen
(74) *Attorney, Agent, or Firm*—Bell, Boyd & Lloyd LLC

(57) ABSTRACT

The present invention is provided for obtaining an apparatus and a method for accurately measuring a variation of a distortion of an optical fiber by excluding an apparent variation of the distortion of the optical fiber which is generated by a drift of a BOTDR waveform. The distortion measuring apparatus of the present invention comprises a sensor cable and a reference fiber which is connected with the sensor cable in series. The measured variation of the distortion of the sensor cable is corrected by subtracting the apparent variation of the distortion of the reference fiber from the measured variation of the distortion of the sensor cable. It is preferable that the reference fiber be housed in an thermostatic chamber and temperature of the reference fiber be maintained in a predetermined value within a range of 10 to 40° C. with an error of ±2° C.

12 Claims, 3 Drawing Sheets

DISTORTION MEASURING APPARATUS AND DISTORTION MEASURING METHOD USING THIS APPARATUS

BACKGROUND OF THE INVENTION

1. Field of the Invention

The present invention relates to a distortion measuring apparatus for measuring variations in distortion generated in an optical fiber using a BOTDR (Brillouin Optical Time Domain Reflectometry) method, and further relates to the distortion measuring apparatus in which an accuracy of the measurement can be improved.

2. Description of the Related Art

In order to monitor anomalies such as a collapse or a landslide of a monitored object such as a ground such as a slope face or a fabric such as an inner face of a tunnel, there are distortion measuring apparatuses for measuring distortions generated in an optical fiber which is laid on the monitored object as a distortion generated in the monitored object using an OTDR method using Brillouin scattered light (BOTDR method).

This type of distortion measuring apparatus comprises a sensor cable which is fixed on the monitored object, and a BOTDR measuring instrument which emits pulsed light into the sensor cable and measures the Brillouin scattered light returned from the sensor cable. The distortion generated in the monitored object is measured by the distortion measuring apparatus in accordance with the following process.

When the pulsed light which is emitted by the BOTDR measuring instrument is inputted in the optical fiber which is provided in the sensor cable, the light is scattered at a suitable position in the optical fiber and the Brillouin scattered light is generated. In this Brillouin scattered light, the light which is scattered backwardly in the optical fiber (backward scattered Brillouin scattered light) reversely travels in the optical fiber and returns to the BOTDR measuring instrument.

A frequency of the light is varied in compliance with the generation of the Brillouin scattering. When the frequency of the inputted pulsed light is denoted as $v_0$, and a central frequency of the spectrum of the Brillouin scattered light is denoted as $v$, a shift $\delta$ of the frequency of the spectrum of the Brillouin scattered light is denoted as $\delta = v - v_0$. The shift $\delta$ of the frequency of the spectrum of the Brillouin scattered light can also be denoted as a function between the distortion $\epsilon$ of the optical fiber at the position in which the scattering is generated and temperature T. When the temperature T of the optical fiber is constant, the shift $\delta$ of the frequency is denoted as a linear function toward the distortion $\epsilon$ of the optical fiber as shown in a following equation 1.

$$\delta = \delta(0) + C \cdot \epsilon \quad \text{Equation 1}$$

In the equation 1, a symbol $\delta(0)$ denotes the shift of the frequency when the distortion of the optical fiber is zero, and a symbol C denotes a proportion constant which is logically determined or determined based on actual measurement.

Furthermore, when the shift of the frequency and the distortion of the optical fiber at a certain point of time are respectively denoted as $\delta_1$ and $\epsilon_1$, and the shift of the frequency and the distortion of the optical fiber at an another point of time are respectively denoted as $\delta_2$ and $\epsilon_2$, the variation of the shift of the frequency $\delta_2 - \delta_1$ and the variation of the distortion $\epsilon_2 - \epsilon_1$ has a relationship as shown in a following equation 2.

$$\delta_2 - \delta_1 = C \cdot (\epsilon_2 - \epsilon_1) \quad \text{Equation 2}$$

Therefore, a relative variation of the distortion of the optical fiber from a certain point of time can be calculated by detecting the backward scattered Brillouin scattered light, measuring the shift of the frequency, and analyzing the result of the measurement. Consequently, the variation of the distortion of the monitored object can be estimated based on the distortion of the optical fiber.

Furthermore, in the BOTDR method, a distance from the BOTDR measuring instrument to the position in which the Brillouin scattering is generated can be calculated from the amount of time from inputting the pulse light into the optical fiber to returning the light which was scattered to the BOTDR measuring instrument. Consequently, the variation of the distortion of the optical fiber can be measured as the position in which the variation of the distortion of the optical fiber is generated, and therefore, the position in which the distortion was generated on the monitored object can be estimated.

Normally, measured data of the distortion obtained by the BOTDR method is described as a graph (BOTDR waveform) in which a horizontal line denotes the distance from the BOTDR measuring instrument, and a vertical line denotes the distortion of the optical fiber. In this graph, it is necessary to determine the above-described $\delta(0)$ in order to find an absolute amount of the distortion of the optical fiber. However, it is not easy to determine the value of $\delta(0)$, and therefore, the relative variation of the optical fiber which is based on the relative level which is assigned to zero is generally used as the value described along the vertical line of the BOTDR waveform.

However, when the variations of the distortion of the optical fiber in the sensor cable are successively measured several times using the above-described distortion measuring apparatus, there are cases in which the BOTDR waveform drifts up and down. As a result, the true variation of the distortion of the optical fiber cannot be distinguished from the apparent variation of the distortion of the optical fiber which is generated by the drift of the BOTDR waveform, and therefore, the distortion cannot be measured accurately. In particular, when the BOTDR measuring instrument is switched ON/OFF or when a plurality of channels in which each channel is connected with the sensor cable are connected with the BOTDR measuring instrument and are switched, relatively large drifts tend to be generated.

SUMMARY OF THE INVENTION

An object of the present invention is, therefore, providing an apparatus and a method in which an accurate measurement of the variation of the distortion of the optical fiber can be performed by excluding the apparent variation of the distortion of the optical fiber which is generated by the drift of the BOTDR waveform.

The above-described object is achieved by using a distortion measuring apparatus comprising a sensor cable and a reference fiber which is connected with the sensor cable in series, and by subtracting the apparent variation in the distortion of the reference fiber from a measured variation of the distortion of the sensor cable in order to correct the measured variation of the distortion of the sensor cable.

It is preferable that the reference fiber be housed into an thermostatic chamber and that the temperature of the reference fiber be maintained at a predetermined value within a range of 10 to 40° C. with an error within ±2C.

It is further preferable that the reference fiber be bundled in a free-coil shaped having a diameter of 20 to 30 cm and be placed on a stationary place for preventing an appearance of a lateral pressure in order to avoid a further variation of the distortion of the reference fiber generated by an external force.

It is further preferable that the length of the reference fiber be not less than 20 meters in order to distinguish the position of the reference fiber in the BOTDR waveform.

Furthermore, when the reference fiber is provided between the sensor cable and the BOTDR measuring instrument of the distortion measuring apparatus, if a plurality of channels in which each channel is connected with the sensor cable connected with the BOTDR measuring instrument, a plurality of reference fibers provided for these sensor cables can be housed into the same thermostatic chamber, and therefore, the distortion measuring apparatus can be provided economically.

DESCRIPTION OF THE PREFERRED EMBODIMENTS

Preferred embodiments will be presented in the following with reference to FIGS. 1 to 4. Those parts that are the same as or similar to the conventional parts are given the same reference numbers.

Figure 1:
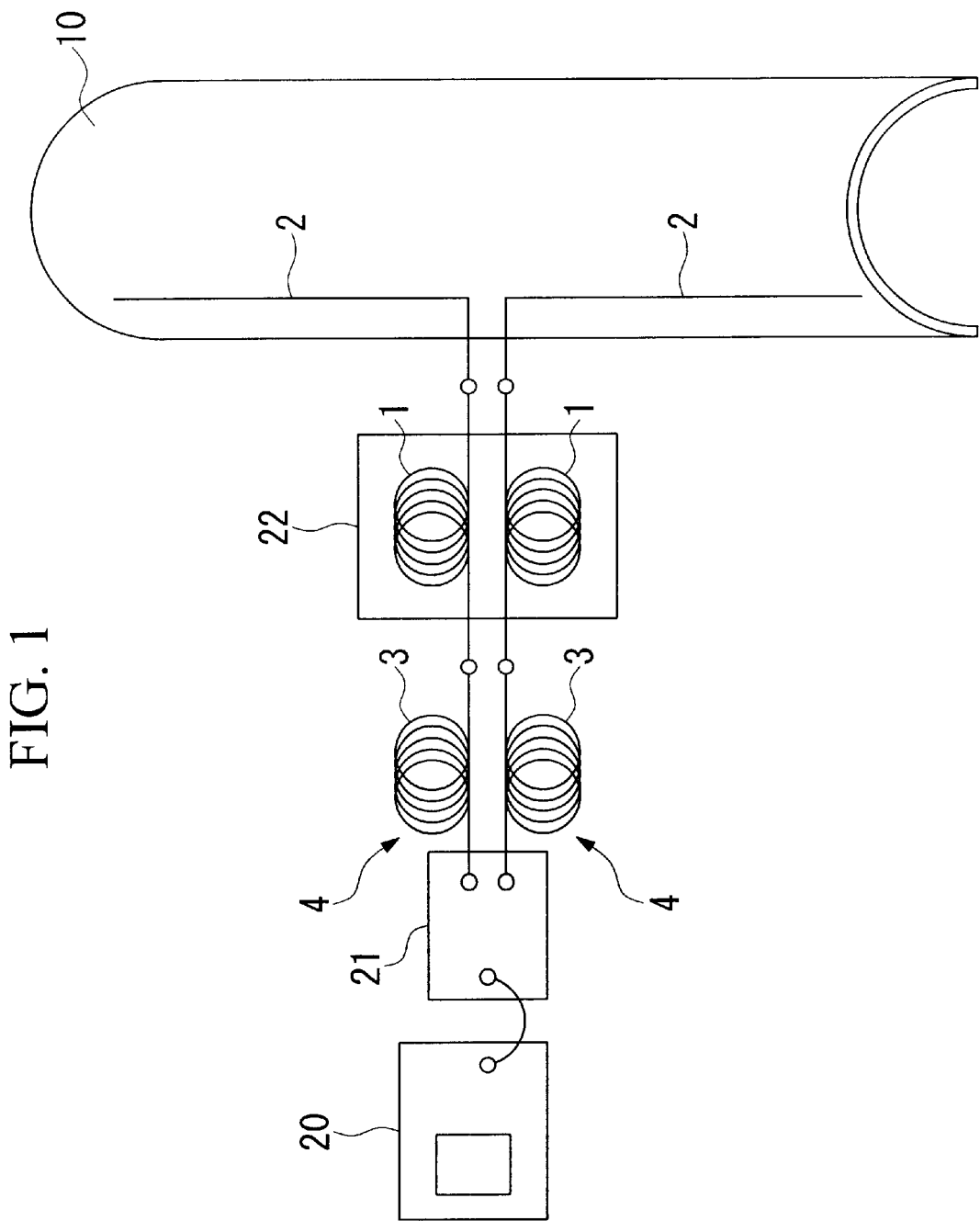
FIG. 1 is a schematic diagram of an embodiment of the distortion measuring apparatus of the present invention.
Figure 2:
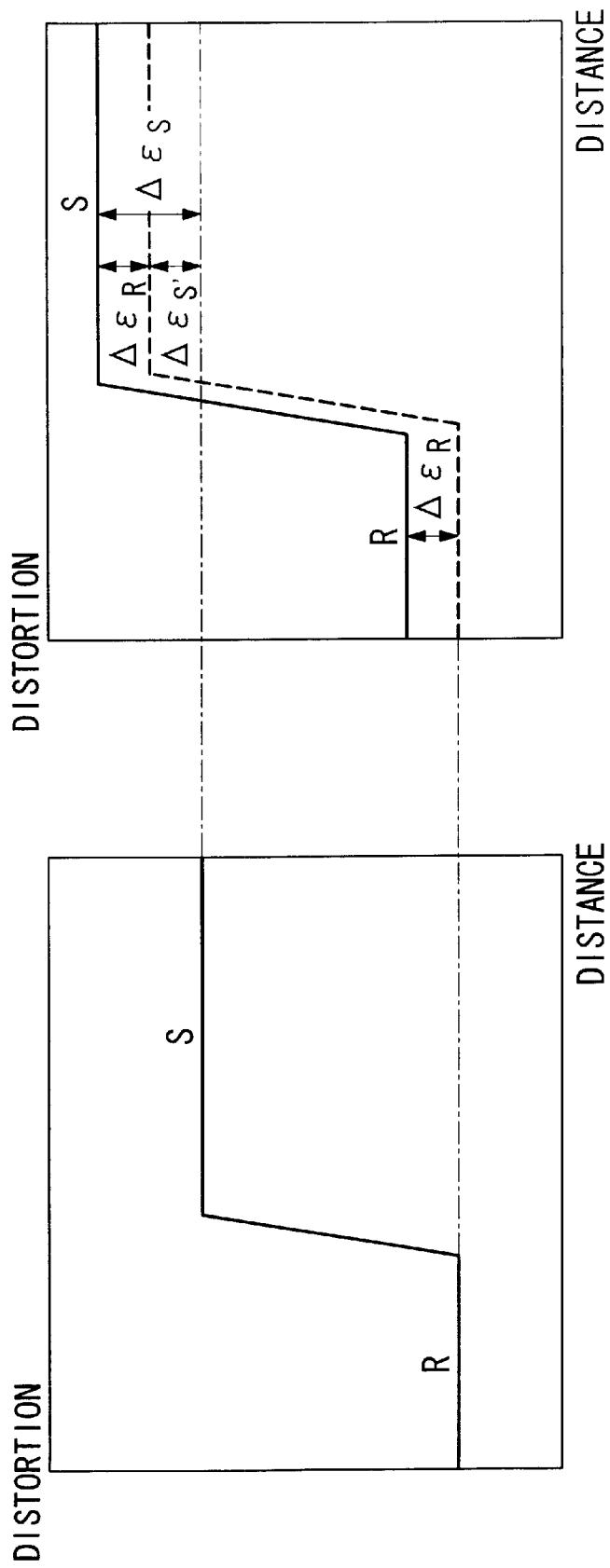
FIG. 2A is a graph which shows an embodiment of the BOTDR waveform obtained by the distortion measuring apparatus of the present invention.
FIG. 2B is a graph which shows an embodiment of the BOTDR waveform obtained by the distortion measuring apparatus of the present invention.

FIG. 1 shows an embodiment of the distortion measuring apparatus of the present invention. In FIG. 1, reference numeral 20 denotes a BOTDR measuring instrument. The BOTDR measuring instrument is connected with a channel selector 21.

The channel selector 21 is connected with a plurality of channels 4, and the channel 4 which is accessed with the BOTDR measuring instrument can be switched by the channel selector 21 when the measurement is performed. Furthermore, each channel 4 is composed of a dummy fiber 3, a reference fiber 1, and a sensor cable 2, and is connected with an optical connector in series in this order from the channel selector 21 side.

The reference fiber 1 is housed in a thermostatic chamber 22 and the temperature of the reference fiber 1 is maintained uniformly. The sensor cable 2 is closely laid on a monitored object 10.

The distortion measuring apparatus of the present invention is different from the conventional apparatuses in the point that the reference fiber 1 is connected with the sensor cable 2 in series. As a result, when the variation of the distortion of the monitored object 10 is measured continuously, the variation of the distortion of the sensor cable 2 can be corrected based on the variation of the distortion of the reference fiber 1.

The reference fiber 1 must be positioned in a circumstance in which effects of disturbances such as variations in temperature or external forces are avoided during the measurement is continuously performed. That is, as described above, since the shift of the frequency of the Brillouin scattered light is affected by temperature, the shift of the frequency is varied in compliance with the variation of temperature and an apparent variation of the distortion of the reference fiber 1 occurs, and as a result, the distortion of the reference fiber 1 cannot be measured accurately. Therefore, the temperature of the reference fiber 1 must be maintained uniformly using the thermostatic chamber 22 and the like. In this case, the variation in temperature allowed in maintaining the temperature of the reference fiber 1 uniform, can be determined as follows, for example.

When the variation of the temperature $\Delta T(° C.)$ of the reference fiber 1 is occurs, the shift of the frequency of the Brillouin scattered light is varied, and the apparent variation of the distortion occurs. This apparent variation of the distortion (%) is approximately estimated as $0.002 \cdot \Delta T$. Furthermore, the true variation of the distortion of the reference fiber 1 occurs according to a difference of a coefficient of thermal expansion between the optical fiber and a sheath provided thereon caused by the variation of the temperature $\Delta T(° C.)$. Therefore, the apparent variation of the distortion (%) of the reference fiber 1 is approximately estimated as 0.003 to $0.005 \cdot \Delta T$ by adding the effect of the true variation of the distortion.

Usually, in the measurement of the variation of the distortion of the monitored object 10, it is required that 0.01 to 0.02% of the variation of the distortion be measured. In order to measure the variation of the distortion of these extents, it is preferable that the variation of the temperature of the reference fiber 1 be controlled to not more than ±2%, and more preferable, be controlled to not more than ±1%.

A median of the variation of the temperature of the reference fiber 1 is not limited; however, in order to restrict the effect of expansion and contraction of the sheath, it is preferable that the median is provided within the range of 10 to 40° C.

In order to restrict the effect of expansion and contraction of the sheath caused by the variation of the temperature, it is preferable that the optical fiber having a thin sheath be used as the reference fiber 1. Specifically, an optical fiber having a diameter of 250 μm, a coated optical fiber having a diameter of 0.9 mm, and a coated optical fiber tape, or an optical fiber cord or an optical fiber cable having a diameter of not more than 3 mm can be used as the reference fiber 1. In particular, the optical fiber having a diameter of 250 μm, the coated optical fiber having a diameter of 0.9 mm, and the coated optical fiber tape are preferably used as the reference fiber 1.

In order to avoid a further variation of the distortion of the reference fiber 1, it is preferable that the external force which acting on the reference fiber 1 not be varied during the measurement. Specifically, it is preferable that the reference fiber 1 be bundled in a free-coil shaped having a diameter of 20 to 30 cm and be placed at a stationary place for preventing occurrence of lateral pressure.

The length of the reference fiber 1 must be not less than 2 meters in order to distinguish the position of the reference fiber 1 in the BOTDR waveform. In this case, it is preferable that the length of the reference fiber 1 be not less than 20 meters in consideration of the accuracy of the measurement.

An upper limit of the length of the reference fiber 1 is not defined; however, no new effect is obtained even when the reference fiber 1 is extended over 100 meters. In addition, when the reference fiber 1 is too long, there is the possibility that the Brillouin scattered light which has returned from the sensor cable 2 will be attenuated and the accuracy of the measurement will be deteriorated. Therefore, it is preferable that the length of the reference fiber be not more than 100 meters.

In the embodiment of FIG. 1, the reference fiber 1 is located between the sensor cable 2 and the BOTDR measuring instrument 20; however, the location of the reference fiber 1 is not limited to this so long as it can clearly be recognized. For example, the reference fiber 1 may be located on the middle portion of the sensor cable 2, or may be located on the end portion of the sensor cable 2 which is opposite to the BOTDR measuring instrument 20 side.

When the reference fiber 1 is located between the sensor cable 2 and the BOTDR measuring instrument 20 as shown in FIG. 1, a plurality of reference fibers 1 can be housed in the same thermostatic chamber 22, and therefore, the distortion measuring apparatus can be provided economically.

Furthermore, when the reference fiber 1 is located between the sensor cable 2 and the BOTDR measuring instrument 20, a dead zone in which measurement cannot be performed occurs in a predetermined area adjacent to the BOTDR measuring instrument 20. Hence, it is preferable that the dummy fiber 3 be also provided in compliance with the dead zone. In this case, it is preferable that the length of the dummy fiber 3 be not less than 50 meters.

The variety of the optical fiber which is used as the dummy fiber 3 is not particularly limited; however, the optical fiber of the same kind of the reference fiber 1 can be used.

The dummy fiber 3 and the reference fiber 1 can be integrated into one optical fiber. In this case, it is preferable that the length of the optical fiber which includes the dummy fiber 3 and the reference fiber 1 be not less than 70 meters.

In addition, the optical fiber which includes the dummy fiber 3 and the reference fiber 1 may be bundled in a free-coil shaped and housed in the thermostatic chamber 22.

Next, the distortion measuring method for the monitored object 10 using the distortion measuring apparatus of the present invention will be explained.

FIGS. 2A and 2b are graphs which show an embodiment of the BOTDR waveform obtained by the distortion measuring apparatus of the present invention. In each graph, a horizontal axis denotes a distance from the BOTDR measuring instrument and a vertical axis denotes a variation of the distortion in each position.

When the BOTDR waveforms along a continuous time series as shown in FIGS. 2A and 2B are obtained by measuring the distortion of the same monitored object two times at a predetermined interval, the variation of the distortion of the sensor cable at the position S during the continuous time series shown in FIGS. 2A and 2B is apparently measured as $\Delta\epsilon_s$. Here, when drifting does not occur, it is assumed that the BOTDR waveform shown as a dotted line in FIG. 2B is obtained, however, in reality, the drifting occurring in the BOTDR waveform. Therefore, the variation of the distortion of the sensor cable caused by the distortion which is applied to the sensor cable at the position S should be denoted as $\Delta\epsilon_s{}'$, although this distortion is apparently measured as $\Delta\epsilon_s$ which is the sum of the distortion and the drift.

As a result, in the conventional distortion measuring method, the variation of the distortion cannot be accurately measured since the apparent variation of the distortion which is generated by the drift of the BOTDR waveform cannot be measured.

In contrast, in the distortion measuring apparatus of the present invention, since the reference fiber is provided as described above, the distortion in the BOTDR waveform of the reference fiber at the position R shown in FIGS. 2A and 2B can be measured. This distortion of the reference fiber is estimated to be constant regardless of the time elapsed, and therefore, the variation of distortion of the reference fiber $\Delta\epsilon_R$ can be used as the variation caused by the drift.

Consequently, the true variation of the distortion of the sensor cable $\Delta\epsilon_s{}'$ caused by the distortion which is applied to the sensor cable at the position S can be measured as $\Delta\epsilon_s - \Delta\epsilon_R$, and therefore, the variation of the distortion in which the apparent variation of the distortion which is generated by the drift is excluded can be accurately measured.

Next, an embodiment of the measurement of the distortion using the distortion measuring apparatus of the present invention will be explained.

Firstly, two sensor cables 10 meters in length are fixed on a face of a tunnel provided as a monitored object, and a nylon coated optical fiber having a diameter of 0.9 mm and a length of 100 meters is bundled in a free-coil shaped having a diameter of 20 cm, is connected with one end of each sensor cable as a dummy fiber and a reference fiber. These nylon coated optical fibers are housed in an thermostatic chamber and the temperature of the thermostatic chamber is maintained at 20° C.±2° C. The other end of each nylon coated optical fiber is connected with a channel selector using a connector. Furthermore, the channel selector is connected with a BOTDR measuring instrument, and the distortion measuring apparatus of the present invention is constructed.

Secondly, distortion of the two sensor cable are automatically measured by switching the two channels every 12 hours using the channel selector, and the BOTDR waveforms thereof are obtained.

The measured values of the variation of the distortion are shown in TABLE 1. In TABLE 1, $\Delta\epsilon_s$ denotes in the variation of the distortion of the sensor cable, and $\Delta\epsilon_R$ denotes the variation of the distortion of the reference fiber which are based on a time series 1. Furthermore, $\Delta\epsilon_s - \Delta\epsilon_R$ denotes the reminder of $\Delta\epsilon_R$ subtracted from $\Delta\epsilon_s$, and also denotes the variation the distortion of the sensor cable which is corrected by the variation the distortion measuring apparatus of the present invention

TABLE 1

| TIME SERIES | CHANNEL 1 | | | CHANNEL 2 | | |
|---|---|---|---|---|---|---|
| | $\Delta\epsilon_S$ | $\Delta\epsilon_R$ | $\Delta\epsilon_S - \Delta\epsilon_R$ | $\Delta\epsilon_S$ | $\Delta\epsilon_R$ | $\Delta\epsilon_S - \Delta\epsilon_R$ |
| 1 | 0 | 0 | 0 | 0 | 0 | 0 |
| 2 | −0.02 | −0.02 | 0 | 0.01 | 0.01 | 0 |
| 3 | 0.03 | 0.03 | 0 | −0.01 | −0.01 | 0 |
| 4 | 0 | 0 | 0 | 0.02 | 0.002 | 0 |
| 5 | −0.01 | −0.01 | 0 | 0.03 | 0.03 | 0 |
| 6 | 0.01 | 0.01 | 0 | 0.04 | 0.03 | 0.01 |
| 7 | −0.01 | −0.01 | 0 | 0 | −0.02 | 0.02 |
| 8 | −0.03 | −0.03 | 0 | 0.01 | −0.01 | 0.02 |
| 9 | 0.02 | 0.02 | 0 | 0.03 | 0.01 | 0.02 |
| 10 | 0.01 | 0.01 | 0 | 0.01 | −0.03 | 0.04 |
| 11 | −0.01 | −0.01 | 0 | 0.02 | −0.02 | 0.04 |

TABLE 1-continued

| TIME | CHANNEL 1 | | | CHANNEL 2 | | |
|---|---|---|---|---|---|---|
| SERIES | $\Delta\epsilon_S$ | $\Delta\epsilon_R$ | $\Delta\epsilon_S-\Delta\epsilon_R$ | $\Delta\epsilon_S$ | $\Delta\epsilon_R$ | $\Delta\epsilon_S-\Delta\epsilon_R$ |
| 12 | 0.02 | 0.02 | 0 | 0 | −0.04 | 0.04 |
| 13 | 0.03 | 0.03 | 0 | 0.01 | −0.05 | 0.06 |

Note: $\Delta\epsilon_S$, $\Delta\epsilon_R$, and $\Delta\epsilon_S-\Delta\epsilon_R$ are given in units of %.

Figure 3:
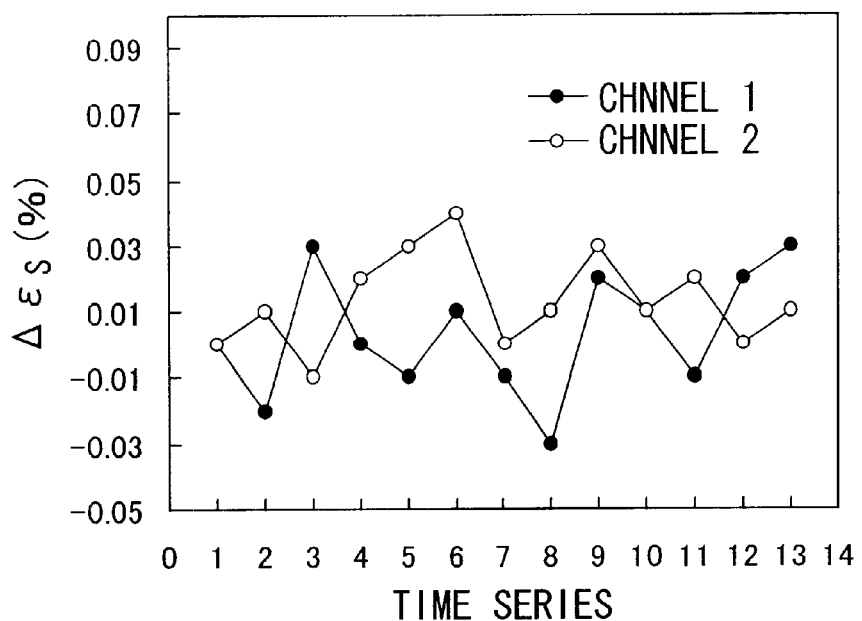
FIG. 3 is a graph which shows an embodiment of a measured variation of the distortion of the optical fiber.
Figure 4:
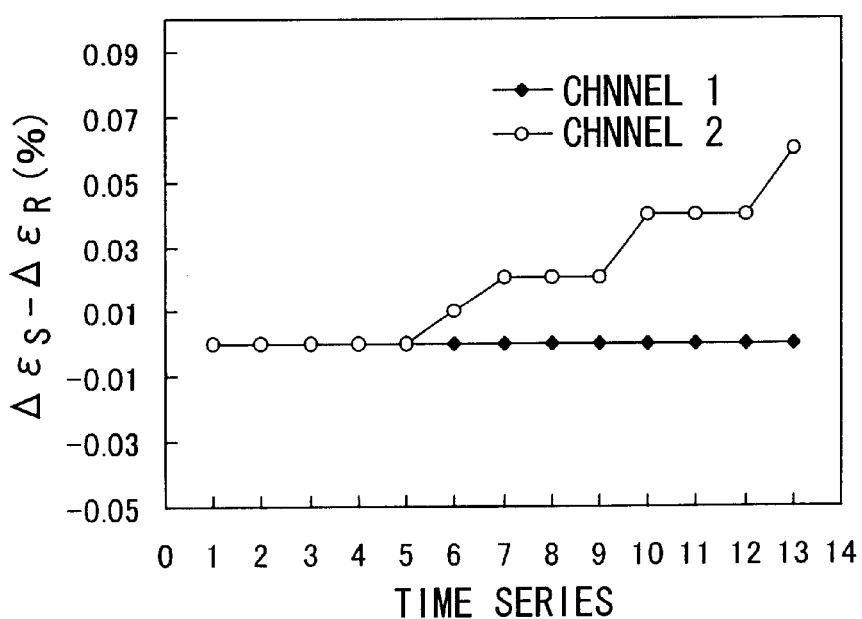
FIG. 4 is a graph which shows an embodiment of a measured variation of the distortion of the optical fiber which is corrected by a distortion measuring method of the present invention.

FIGS. 3 and 4 show the variation of the $\Delta\epsilon_s$ and $\Delta\epsilon_s-\Delta\epsilon_R$ over time. Since the $\Delta\epsilon_s$ is effected by the drift, the distortion caused in the sensor fiber cannot be measured accurately from the $\Delta\epsilon_s$.

In contrast, when the $\Delta\epsilon_s-\Delta\epsilon_R$ in which the apparent variation of the distortion which is generated by the drift in the BOTDR waveform is excluded, the distortion caused in the sensor fiber can be accurately measured.

What is claimed is:

1. A distortion measuring apparatus which measures a variation of distortion of a monitored object using a BOTDR (Brillouin Optical Time Domain Reflectometry) method, the distortion measuring apparatus comprising:
a sensor cable which is fixed on the monitored object at a distal end thereof, and
a BOTDR measuring instrument which emits pulsed light into the sensor cable and measures the Brillouin scattered light returned from the sensor cable;
wherein a reference fiber is connected with a proximal end of said sensor cable in series, and
a dummy fiber is provided between said BOTDR measuring instrument and a proximal end of said reference fiber.

2. A distortion measuring apparatus according to claim 1, wherein said reference fiber is housed in an thermostatic chamber and a temperature of said reference fiber is maintained in a predetermined value within a range of 10 to 40° C. with an error of ±2° C.

3. A distortion measuring apparatus according to claim 1, wherein said reference fiber is bundled in a free-coil shaped having a diameter of 20 to 30 cm.

4. A distortion measuring apparatus according to claim 1, wherein the length of said reference fiber is not less than 20 meters.

5. A distortion measuring apparatus according to claim 1, wherein said reference fiber is provided between said sensor cable and said BOTDR measuring instrument.

6. A distortion measuring apparatus according to claim 1, wherein the length of said dummy fiber is not less than 50 meters.

7. A distortion measuring method using a distortion measuring apparatus which measures a variation of distortion of a monitored object using a BOTDR (Brillouin Optical Time Domain Reflectometry) method, the distortion measuring apparatus comprising:
a sensor cable which is fixed on the monitored object at a distal end thereof;
a BOTDR measuring instrument which emits pulsed light into the sensor cable and measures the Brillouin scattered light returned from the sensor cable;
a reference fiber which is connected with a proximal end of said sensor cable in series; and
a dummy fiber which is provided between said BOTDR measuring instrument and a proximal end of said reference fiber; and
the distortion measuring method comprising a step of:
subtracting an apparent variation of a distortion of said reference fiber from the variation of the distortion of said sensor cable to correct the variation of the distortion of said sensor cable.

8. A distortion measuring method according to claim 7, wherein said reference fiber is housed in a thermostatic chamber and a temperature of said reference fiber is maintained in a predetermined value within a range of 10 to 40° C. with an error of ±2° C.

9. A distortion measuring method according to claim 7, wherein said reference fiber is bundled in a free-coil shaped having a diameter of 20 to 30 cm.

10. A distortion measuring method according to claim 7, wherein the length of said reference fiber is not less than 20 meters.

11. A distortion measuring method according to claim 7, wherein said reference fiber is provided between said sensor cable and said BOTDR measuring instrument.

12. A distortion measuring method according to claim 7, wherein the length of said dummy fiber is not less than 50 meters.

* * * * *